United States Patent [19]
Mochizuki et al.

[11] Patent Number: 5,840,561
[45] Date of Patent: Nov. 24, 1998

[54] PHYTASE

[75] Inventors: Daisuke Mochizuki; Junko Tokudo; Tadashi Suzuki, all of Mobara; Masao Shimada, Yamato; Shin-ichirou Tawaki, Kawasaki, all of Japan

[73] Assignee: Mitsui Chemicals, Inc., Tokyo, Japan

[21] Appl. No.: 977,060

[22] Filed: Nov. 24, 1997

Related U.S. Application Data

[62] Division of Ser. No. 498,263, Jul. 3, 1995.

[30] Foreign Application Priority Data

| Jul. 5, 1994 | [JP] | Japan | 6-174906 |
| Feb. 24, 1995 | [JP] | Japan | 7-60111 |

[51] Int. Cl.⁶ .............................. C12N 9/20; C12N 1/20; C12N 15/00; C07H 21/04
[52] U.S. Cl. ................. 435/195; 435/196; 435/252.3; 435/320.1; 435/18; 536/23.2
[58] Field of Search .................... 435/195, 196, 435/252.3, 320.1, 18; 536/23.2

[56] References Cited

FOREIGN PATENT DOCUMENTS

WO94/03072  2/1994  WIPO .

OTHER PUBLICATIONS

Nayini et al, The Phytase of Yeast, *Lebensmittel Wissenschaft und Technologie*, vol. 17, No. 1, 1984, pp. 24–26 (XP–002054007).

Lambrechts et al, "Utilization of Phytase by Some Yeasts", *Biotechnology Letters*, vol. 14, No. 1, Jan. 1, 1992, pp. 61–66 (XP–002053185).

Segueilha et al, "Reduction of Phytate Content in Wheat Bran and Glandless Cotton Flour by *Schwanniomyces castelli*", *Journal of Agricultural and Food Chemistry*, vol. 41, No. 12, Dec. 1993, pp. 2541–2454 (XP–002053184).

Sequeilha et al, "Purification and Properties of the Phytase from *Schwanniocyes castelli*", *Journal of Fermentation and Bioengineering*, vol. 74, No. 1, 1992, pp. 7–11 (XP–002053183).

Yamada et al, "Production, Purification and Some General Properties of the Enzyme", *Agricultural and Biological Chemistry*, vol. 32, No. 7, Jul 1968, pp. 1275–1282 (XP–002053182)

*Primary Examiner*—Keith D. Hendricks
*Assistant Examiner*—Tekchand Saidha
*Attorney, Agent, or Firm*—Burns, Doane, Swecker & Mathis, L.L.P.

[57] ABSTRACT

A novel phytase is disclosed. The phytase consists essentially of a single type of subunits, and can hydrolyze a phytate to myo-inositol. A gene encoding the phytase, which is originated from *Schwanniomyces occidentalis* is also disclosed.

13 Claims, 9 Drawing Sheets

PHYTASE

This application is a divisional of application Ser. No. 08/498,263, filed Jul. 3, 1995.

BACKGROUND OF THE INVENTION

I. Field of the Invention

The present invention relates to a novel phytase, a gene encoding the same, a recombinant vector containing the gene, a microorganism transformed with the recombinant vector, and a method for converting a phytate into myo-inositol using the phytase produced by the transformant.

II. Description of the Related Art

Phytase is a phosphatase which dephosphorylates phytic acid. The phytase which hydrolyzes the phosphate at 6-position is called 6-phytase (EC. 3.1.3.2.6.) and the phytase which hydrolyzes the phosphate at 3-position is called 3-phytase (EC. 3.1.3.8.). The one which is called simply "phytase" means 6-phytase. Phytase occurs in higher plants, animals and microorganisms. For example, phytases originated from higher plants such as Mung bean (N. C. Mandal et al., Phytochemistry, vol. 11: pp.495–502, (1972)) and wheat (P. E. Lim et al., Biochemica et Biophysica Acta, vol. 302: p.316–328, (1973)); phytases originated from microorganisms such as Pseudomonas (G. C. J. Irving et al., Aust. J. Biol. Sci., vol. 24: pp.547–557, (1971)), *Bacillus subtilis* (V. K. Paver et al., J.Bacterial., vol. 151: pp.1102–1108, (1982)), Klebsiella (Varsha Shah et al., Indian Journal of Biochemistry and Biophysics, vol. 27: pp.98–102, (1990)), Aspergillus (Abul H. J. Ullah et al., Preparative Biochemistry, vol. 17: pp.63–91, (1987)) (European Patent Publication Nos. 0 321 004 and 0 420 358, European patent application No. 92-200414, WO9403612), and *Schwanniomyces castelli* CBS 2863 (P. Galzy et al., J. Ferment. Bioeng., vol. 74.1: pp.7–11, (1992)) are known. It should be noted that *Schwaniiomyces castelli* CBS 2863 is now classified into *Schwanniomyces occidentalis* IFO 1840 (Kregerm van Rij et al.: the yeast, a taxonomic study, 3rd ed., Elsevier Sci. Publisher, Amsterdam, The Netherlands, (1984)) (LIST OF CULTURE MICROORGANISMS, 9th ed.: Institute for Fermentation Osaka, pp75–76, (1992)).

Phytic acid (inositol hexakisphosphate) which is the substrate of phytase is hexaphosphate of myo-inositol (hereinafter also referred to as simply "inositol"). Phytin which is calcium-magnesium mixed salt of phytic acid is contained in all kinds of nuts, cereals, beans, seeds, spores and pollens in an amount of 1–3% as a major reserve substance of phosphate (E. Graf et al., J. Am. Oil. Chem. Soc., vol. 60: pp.1861–1867, (1983)).

Pollution of rivers and the like by the phosphate in excrements of cattle (animals having one stomach) which are bred using feed containing large amount of cereals and seeds is now problematic. As a countermeasure therefor, it is now tried to reduce the concentration of phosphate source in excrements by blending phytase in the feed as a feed additive, thereby decomposing phytate in the feed by the phytase.

However, known phytases lose their activities by 40% after treatment at 68° C. for 10 minutes (Abul H. J. Ullah et al., Preparative Biochemistry, vol. 18: pp.483–489, (1988)). Therefore, most activity of phytase is lost under the temperature (75°–85° C.) at which the feed is molded. Thus, feed cannot be molded or drying step of the feed should be largely changed.

On the other hand, it is tried to produce myo-inositol by using phytase. Myo-inositol is conventionally produced by extracting phytin from corn steep liquor or rice bran and hydrolyzing the extracted phytin at high temperature under high pressure. However, hydrolysis of phytin requires special equipment and large energy, so that its production cost is high.

To overcome this problem, it was proposed to produce inositol by using an enzyme which can hydrolyze phytate at normal temperature under normal pressure. Hydrolysis of phytin by using a microorganism belonging to genus Aspergillus (Abul H. J. Ullah et al., Preparative Biochemistry, vol. 18: pp.483–489, (1988)) or *Schwanniomyces occidentalis* (supra) has been reported.

However, among the enzymes catalyzing hydrolysis of phytin, the phytase produced by a microorganism belonging to genus Aspergillus can hydrolyze phytic acid or salts thereof into inositol monophosphate, but further hydrolysis, that is, hydrolysis into myo-inositol cannot be attained by this enzyme. Therefore, to carry out the hydrolysis into myo-inositol, it is necessary to employ another enzyme such as acid phosphatase together with the phytase. This is not preferred in view of economy.

Recently, it was discovered that *Schwaniiomyces occidentalis* produces a phytase which can completely decompose sodium phytate to myo-inositol, of which thermal stability is relatively high, 74° C.

In general, since phytase is a kind of phosphatases, its production is induced by culturing a microorganism in a medium having a low concentration of phosphate in order to release the negative control of the production of the enzyme, or by culturing the microorganism in a medium containing a phytate as a sole phosphate source in order to promote the positive control of the production. P. Galzy et al. (supra) continuously cultured *Schwaniiomyces occidentalis* employing a chemstat in order to keep the concentration of phosphate in the culture medium low. However, the amount of the secreted phytase is as low as 0.15 mg/l. To increase production of the enzyme, one of ordinary skill in the art may consider to produce the enzyme by genetic engineering. However, the gene encoding phytase has not been identified. Further, since phytase is a tetramer containing two types of subunits, that is, subunit α (125 kD) and β (70 kD) (α:β=1:3) according to P. Galzy et al. (supra), in order to produce the enzyme in a large amount by using genetic engineering, it is necessary to express two types of subunits in a single cell. This requires highly sophisticated genetic engineering method because two kinds of genes encoding the two kinds of subunits, respectively, must be regulated. Further, formation of a molecule having a high-order (4-order) structure in a host cell is not preferred.

SUMMARY OF THE INVENTION

Accordingly, an object of the present invention is to provide a novel phytase which can hydrolyze phytic acid or a salt thereof into myo-inositol, which has a simple structure so that it can be produced by a genetic engineering process.

Another object of the present invention is to provide a cloned gene encoding the above-mentioned gene according to the present invention, a recombinant vector containing the gene, and a microorganism transformed with the recombinant vector.

Still another object of the present invention is to provide a method for converting phytate into myo-inositol using the cells, treated cells or a culture medium containing the cells of the transformed microorganism.

That is, the present invention provides a phytase consisting essentially of a single type of subunits, which can hydrolyze a phytate to myo-inositol. The present invention also provides a cloned gene originated from *Schwaniiomyces occidentalis*, which encodes a phytase subunit having a molecular size after removing sugar chains of 50 kD±5 kD determined by SDS-polyacrylamide gel electrophoresis. The present invention further provides a recombinant vector containing the gene according to the present invention, which recombinant vector can express said gene in a host cell. The present invention still further provides a microorganism transformed with the recombinant vector according to the present invention. The present invention still further provides a method for converting a phytate into myo-inositol comprising contacting the phytate with the phytase according to the present invention.

Since the phytase according to the present invention can hydrolyze phytates into myo-inositol, another enzyme such as acid phosphatase is not required to hydrolyze phytates into myo-inositol, which is advantageous from the view point of economy. Since the phytase according to the present invention has only one kind of polypeptide in contrast with the known phytase having two kinds of polypeptides, it is easier to produce the enzyme by genetic engineering. The gene encoding the phytase of the present invention was first cloned and sequenced. A recombinant vector containing the gene and a microorganism transformed with the recombinant vector, which produces the phytase according to the present invention in a large amount were first provided by the present invention. Thus, efficient production of myo-inositol in a large amount was first attained by the present invention.

Further, the phytase according to a preferred mode of the present invention has high optimum temperature and high heat resistance, so that enzyme reaction at a temperature which cannot hitherto be carried out can be achieved. Since the gene encoding the phytase according to the present invention was first provided, the present invention will contribute to preparation of phytases (second generation enzymes) having characteristics different from those of the phytase according to the present invention (in terms of optimum pH, optimum temperature, heat resistance, stability to solvents, specific activity, affinity to substrate, secretion ability, translation rate, transcription control and the like). Further, the cloned gene according to the present invention may be employed for screening of phytases having the similar characteristics.

BEST MODE FOR CARRYING OUT THE INVENTION

Figure 1:
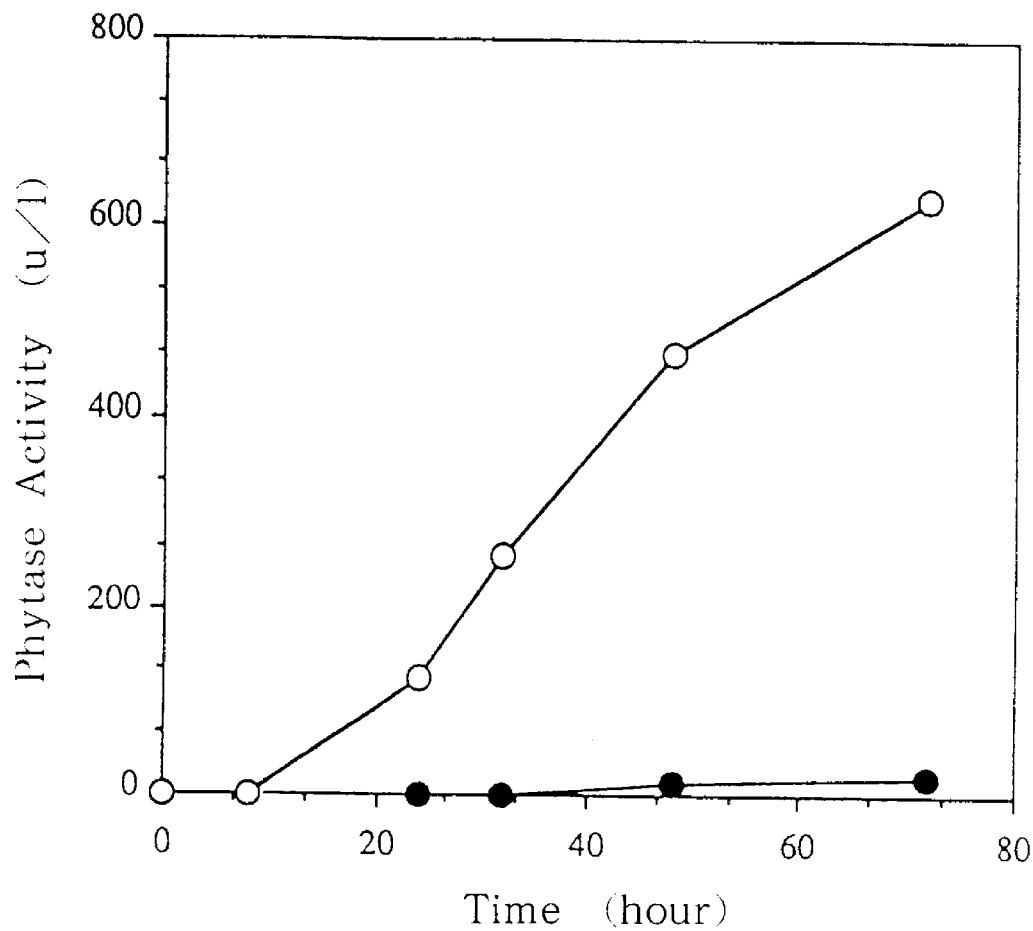
FIG. 1 shows change of phytase activity of culture medium of *Schwaniiomyces occidentalis* with time.

The phytase according to the present invention can hydrolyze phytates into myo-inositol. That is, it can completely hydrolyze the 6 phosphate groups attached to phytic acid.

The phytase according to the present invention consists essentially of a single kind of subunits.

An example of the phytase according to the present invention is the phytase originated from *Schwaniiomyces occidentalis*. This phytase is a glycoprotein.

The subunit constituting the phytase originated from *Schwaniiomyces occidentalis* has a molecular size after removal of sugar chains of 50 kD±5 kD, which is determined by SDS-PAGE. The subunit contains at least the sequence shown in SEQ ID NO. 1 and/or SEQ ID NO. 2.

It is thought that the phytase originated from *Schwaniiomyces occidentalis* consists essentially of 3–5 subunits (the subunits are the same each other), usually 4 subunits.

The phytase originated from *Schwaniiomyces occidentalis* has good heat resistance. That is, the phytase has a residual activity of about 90% after treatment at 70° C. for 30 minutes and about 50% after treatment at 75° C. for 30 minutes. The good heat resistance is advantageous in using the enzyme as a feed additive as the feed can be molded at a high temperature.

Production of the phytase originated from *Schwaniiomyces occidentalis* is induced by culturing the yeast in a medium containing calcium salt of a weak acid and a low concentration of phosphate source. The weak acid may preferably be those acid with which the pH of aqueous solution of the calcium salts thereof is not less than 5.0, more preferably not less than 5.5. As the weak acid, carbonic acid is best preferred. The concentration of the calcium salt of the weak acid may usually be 0.01–1% by weight, preferably 0.05–0.5% by weight. The term "low concentration" of the phosphate source in the medium herein means 1 to 6000 mg/l, preferably 1 to 600 mg/l. By culturing *Schwaniiomyces occidentalis* under the inductive conditions described above, the phytate is secreted and accumulated in the culture medium.

The cause of the inductive secretion of the phytase originated from *Schwaniiomyces occidentalis* is not clear. However, the present inventors discovered that when the yeast is cultured in a medium containing a phytate as a sole phosphate source, the phytase activity is scarcely detected in the culture medium, while by adding a calcium salt, the phytase activity is prominently increased. Thus, it is thought that the reason why the production of phytase is induced by calcium salt may be that the suppression of phytase gene by the phosphate liberated in a small amount by decomposition of phytin is cancelled by the calcium salt.

The gene encoding the subunit of the phytase originated from *Schwaniiomyces occidentalis* may be cloned by various methods. However, in view of the fact that yeast is a eukaryote and so the gene may contain introns, it is preferred to clone cDNA prepared from the mRNA of the gene. More particularly, for example, cDNAs prepared from mRNAs of *Schwaniiomyces occidentalis* are inserted into an expression vector for *E. coli* to prepare a cDNA library, and the desired clone may be obtained by selecting a clone specifically reacts with an antibody to the subunit as a probe. An example of this process is detailed in the examples described below.

The cDNA encoding the subunit of the phytase originated from *Schwaniiomyces occidentalis* has a length of 1631 bp, of which sequence is shown in SEQ ID NO. 5. This sequence contains the nucleotide sequences shown in SEQ ID NOs. 3 and 4.

It is well-known in the art that there are cases wherein the activity of an enzyme is retained even if the amino acid sequence of an enzyme is modified to a small extent, that is, even if one or more amino acids in the amino acid sequence are substituted or deleted, or even if one or more amino acids are added to the amino acid sequence. In view of the fact that such modifications of the amino acid sequence can be easily carried out by, for example, site-specific mutagenesis, it is intended that the enzymes as well as the cloned genes encoding the enzymes which have the same amino acid sequence shown in SEQ ID NO. 5 except that one or more amino acids in the amino acid sequence are substituted or deleted, or one or more amino acids are added are within the scope of the present invention as long as the resulting enzyme is within the definition of the present invention, that is, the enzyme can hydrolyze a phytate to myo-inositol and the enzyme consists essentially of a single type of subunits.

The cloned gene encoding the subunit of the phytase originated from *Schwaniiomyces occidentalis* may be expressed in a host other than *Schwaniiomyces occidentalis* by inserting the gene into a vector replicable in the host cell to obtain a recombinant vector and transforming the host cell with the recombinant vector. An example of the recombinant vector containing the gene encoding the subunit of the phytase originated from *Schwaniiomyces occidentalis* is YEpGHP 1 (FIG. 8) which was prepared in the example described below.

The desired clone may also be obtained by partially digesting the genome of *Schwaniiomyces occidentalis*, preparing a genome library therefrom, and selecting the clone which hybridizes with the above-mentioned cDNA encoding the subunit of the phytase originated from *Schwaniiomyces occidentalis*.

By transforming an appropriate host with the recombinant vector containing the gene encoding the subunit of the phytase originated from *Schwaniiomyces occidentalis*, the gene can be expressed and the phytase can be produced in the host cells, which may be secreted.

To express the gene encoding the subunit of the phytase originated from *Schwaniiomyces occidentalis*, it is preferred to utilize a host-vector system by which an exogenous protein can be produced in a host cell. Thus, it is advantageous to utilize the host-vector system employing as the host *E. coli, Bacillus subtilis*, a yeast or a mold fungus. The gene may be expressed by ligating the gene at a downstream site of a promoter and preferably a secretion signal which are known to be effective in the host cell, inserting the resultant into an expression vector replicable in the host cell, and transforming the host cell with the recombinant vector. Alternatively, the gene ligated to the promoter and the secretion signal may be inserted into the chromosome of the host cell. It should be noted that the gene may be inserted into an expression vector which preliminarily has the above-mentioned promoter and the secretion signal.

The present inventors succeeded in producing the phytase originated from *Schwaniiomyces occidentalis* by inserting the genome DNA fragment from this yeast into a vector plasmid YEp24 for *Saccharomyces cerevisiae* and transforming *Saccharomyces cerevisiae* with the prepared recombinant plasmid.

As described in the examples below, the present inventors succeeded in preparing transformants which secrete the phytase originated from *Schwaniiomyces occidentalis* by the method described above, which transformants are *Escherichia coli* MT-10743 and *Saccharomyces cerevisiae* MT-40539. These transformants have been deposited under the Budapest Treaty, the details of the depositions being described in the examples below.

The transformants may be cultured by an ordinary culturing method for the microorganism.

Although the culture medium for the transformants is not restricted and any culture media may be employed which are suited for the microorganism, it is preferred to add calcium salt of the above-mentioned weak acid to cancel the suppression of expression of phytase by the liberated phosphate. The preferred concentration of the calcium salt is the same as described above.

The phytase according to the present invention may be produced by culturing the transformants under normal conditions. To use the phytase for various uses, the culture medium, cells and treated cells may be used as the source of the phytase. The treated cells include cell debris obtained by disrupting the cells by self digestion, by lysation by an organic solvent, by ultrasonic disruption or by homogenization; the above-mentioned cell debris which was partially purified; phytase protein separated from the culture medium or the cells; and the materials in which the cells obtained by culturing or the phytase protein separated from the cells or the culture medium are immobilized in a carrier such as sodium alginate, K-carrageenan or polyacrylamide.

The phytase according to the present invention may be employed as an enzyme source for various uses, such as, for example, feed additive and production of inositol.

A phytate may be converted into myo-inositol by adding the above-mentioned phytase source to a buffer solution containing a phytate such as calcium phytate, and carrying out the reaction. The reaction may be carried out, for example, at 5° to 90° C. for 1 hour to 1 week. The concentrations of the phytate and the phytase may be, for example, 0.02 mg/l to 200 g/l and 0.1 mg/l to 10 g/l, respectively.

EXAMPLES

The present invention will now be described in more detail by way of examples. It should be noted that the examples are presented for the illustration purpose only and should not be interpreted in any restrictive way.

Example 1

Induction of High Expression of Phytase Gene by Addition of Calcium Carbonate

A medium containing, per one liter, 10 g of glucose, 3 g of $(NH_4)_2SO_4$, 0.5 g of $MgSO_4$, 0.5 g of KCl, 0.1 g of $CaCl_2$, 0.135 g of $FeCl_3$, minor metals, vitamins other than inositol, 0.03 g of yeast extract for initial growth, 0.6 g of calcium phytate as a sole phosphate source, and 1 g of $CaCO_3$ for induction of high expression of phytase gene, was prepared. Thirty milliliters of this medium was placed in an Erlenmeyer flask equipped with a baffle and *Schwanniomyces occidentalis* IFO 1840 was inoculated to the medium, followed by culturing the medium at 28° C. for 2 days. As a control, the same procedure as mentioned above was carried out except that the medium did not contain $CaCO_3$.

After the culture, the culture medium was 10-fold concentrated by ultrafiltration using Amicon Centricon 30 microconcentrator, followed by dialysis against deionized water at 4° C. for 2 hours 4 times. The phytase activity of the dialyzed liquid was measured as follows. That is, 900 $\mu$l of an aqueous solution of the substrate (60 mM sodium acetate buffer (pH4.4) containing 5 mM sodium phytate) was added to 100 $\mu$l of the dialyzed liquid and reaction was allowed to occur at 70° C. for 30 minutes. The reaction was stopped by adding 100 $\mu$l of 5N $H_2SO_4$ in the reaction mixture. As a control, the same procedure was carried out except that 100 $\mu$l of 5N $H_2SO_4$ was added to the substrate solution before the reaction. After stopping the reaction, the reaction mixture was diluted in a serial fashion from 1 to 2048-fold in wells of a 96-well microtiter plate. Phosphate-detecting solution (solution A: 1.47 g/l of Malachite Green, 20% $H_2SO_4$; solution B: 7.5% ammonium molybdate; solution C: 11% (w/v) of Tween 20; the solutions A, B and C were mixed at a ratio of 50:12.5:1 immediately before use) was added in an amount of 50 $\mu$l per 100 $\mu$l of the diluted solution, and the mixture was shaken for 30 minutes, followed by measurement of absorbance at 620 nm. Based on a calibration curve in a range of 1–10 nM of phosphate, the amount of released phosphate was calculated from the measured value. One unit of phytase activity was defined as the activity by which 1 $\mu$mol of phosphate is released per minute. The results are shown in FIG. 1. In FIG. 1, symbol "○" shows the results wherein $CaCO_3$ was added and symbol "●" shows the results wherein $CaCO_3$ was not added. As is apparent from FIG. 1, phytase activity was detected in the culture medium to which calcium carbonate was added while almost no phytase activity was detected in the culture medium to which calcium carbonate was not added.

Example 2

Measurement of Phytase Activity and Molecular Size (1) Removal of Sugar Chains of Enzyme Purification of the enzyme which was induced under the conditions described above and secreted and accumulated in the medium in Example 1 was tried in order to identify the enzymatic properties of the phytase.

It was confirmed that the enzyme is a glycoprotein by a preliminary experiment, that is, by SDS-PAGE. It is likely that a glycoprotein does not give a clear band in electrophoresis. Thus, in order to obtain a single band in electrophoresis, sugar chains were preliminarily removed by Endoglycosidse H (Endo H, commercially available from Boehringer Mannheim Biochemica). That is, the enzyme was denatured by treatment in a solution containing 10 mM of sodium acetate (pH 5.2), 100 mM of 2-mercaptoethanol and 0.0025% of SDS, the mentioned concentrations being final concentrations, at 95° C. for 5 minutes, and the resultant was slowly allowed to cool to room temperature. Then Endo H was added in an amount of 4 $\mu$U per 1 ng of protein and reaction was allowed to occur at 37° C. overnight.

It should be noted that, in the experiments described below, the samples of which enzyme activities are measured or which are subjected to electrophoresis were treated in a solution containing 10 mM sodium acetate (pH 5.2) to which Endo H is added in an amount of 4 $\mu$U per 1 ng of protein at 37° C. overnight.

(2) Detection of Hydrolyzing Activity of Crude Enzyme and Measurement of Molecular Size The crude enzyme obtained by removing sugar chains by Endo H in Example 2(1) was subjected to Native PAGE. By silver staining and hydrolytic activity staining, a single band which exhibited hydrolytic activity was detected.

The hydrolytic activity staining was carried out by incubating overnight the gel after electrophoresis in a solution containing 0.1% α-naphthylphosphate, 0.2% first garnet GBC salt and 0.6M sodium acetate buffer (pH 5.0). By this staining, a band having hydrolytic activity is stained in black. To confirm the phytase activity of the polypeptide corresponding to the band stained in black, the polypeptide corresponding to the band was reacted with sodium phytate, and generated phosphate and myo-inositol were quantified. As a result, generation of phosphate and myo-inositol was observed.

Figure 5:
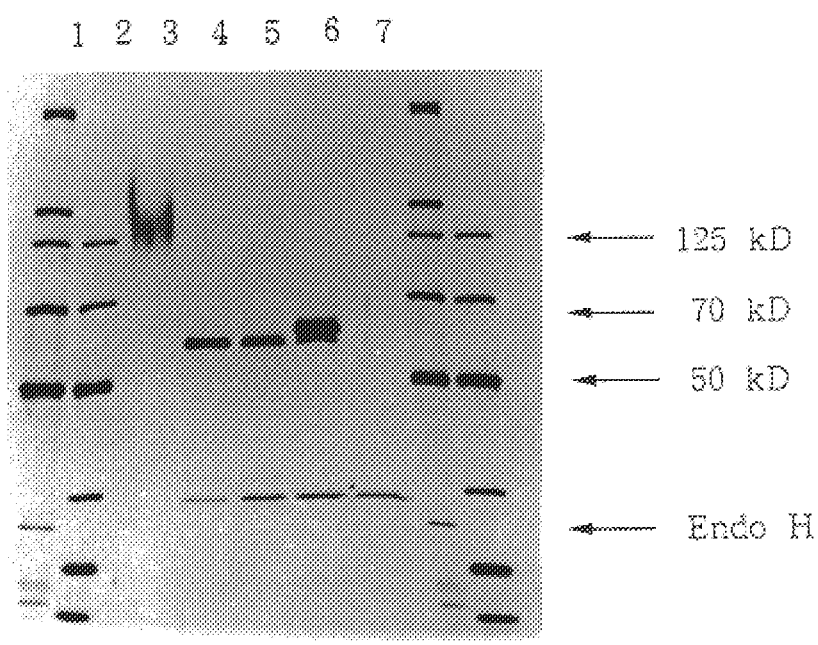
FIG. 5 shows the results of electrophoresis obtained by electrophoresing purified phytase having a molecular size of 50 kD±5 kD originated from *Schwaniiomyces occidentalis* on SDS-polyacrylamide gel.

The molecular size of this polypeptide was measured by SDS-PAGE. The results are shown in FIG. 5. In FIG. 5, lane 1 shows the electrophoretic pattern of molecular size Marker H (commercially available from BIORAD); lane 2 shows the pattern of molecular size Marker L (commercially available from BIORAD); lane 3 shows the pattern of purified enzyme before removal of sugar chains; lane 4 shows the pattern of purified enzyme after removal of sugar chains by the method described in Example 2; lane 5 shows the pattern of purified enzyme after removal of sugar chains by using 20 units of Endo H; lane 6 shows the patter of purified enzyme after removal of sugar chains by using 20 units of Endo H without the denaturing treatment before the reaction with Endo H; and lane 7 shows the pattern of Endo H alone. As can be seen from FIG. 5, the molecular size of the purified subunit is 50 kD±5 kD. Thus, this polypeptide is apparently different from the known α and β subunits of *Schwaniiomyces occidentalis*.

To analyze the enzyme in more detail, the polypeptide was purified (see below) and antibody against the purified polypeptide was prepared by immunizing a rabbit with the polypeptide and purifying the antibody by applying the anti-serum from the rabbit to affinity chromatography (see below). Western blot analysis using this antibody revealed that this antibody reacted with a band corresponding to a molecular size of 50 kD. As mentioned above, the molecular sizes of α and β subunits of the known phytase of *Schwaniiomyces occidentalis* are 125 kD and 70 kD, respectively. In view of the large differences in molecular sizes, it is concluded that the enzyme having phytase activity, which is produced by culturing *Schwaniiomyces occidentalis* in a medium containing calcium carbonate, is a novel enzyme which is different from the known phytase containing α and β subunits.

Example 3

Purification of Phytase from Culture Supernatant

*Schwaniiomyces occidentalis* was inoculated to 20 ml of the medium described in Example 1, and the medium was incubated overnight at 28° C. The whole culture medium was then aseptically added to 2 liters of the same medium and the obtained culture medium was incubated at 28° C. for 2 days. The resultant was centrifuged to obtain about 2 liters of culture supernatant. The obtained culture supernatant was concentrated to 200 ml at 50°–60° C. by an evaporator and the obtained concentrate was dialyzed against 20 mM Tris-HCl buffer at 4° C. for 2 hours 4 times. The resulting dialyzate was concentrated to 20 ml by the evaporator and the obtained concentrate was dialyzed against 20 mM Tris- HCl buffer at 4° C. for 2 hours 4 times. The obtained crude enzyme solution was applied to 10 ml of Q-Sepharose fast flow column (commercially available from Pharmacia) and then the column was washed with 50 ml of 20 mM Tris-HCl buffer, pH 7.5. Elution was performed by passing 20 ml each of 20 mM Tris-HCl buffer containing NaCl at a concentration of 25, 50, 75, 100, 125, 150, 175 or 200 mM in the order mentioned. Fractions were collected every 20 ml and phytase activity of each fraction was measured after dialysis against deionized water at 4° C. for 2 hours 4 times.

The optimum pH, optimum temperature and heat resistance of the obtained enzyme were determined.

The optimum pH of the enzyme was measured by measuring the activity of the enzyme by the method described in Example 1, wherein pH during the measurement of enzyme activity was changed using 20 mM sodium acetate buffer or 20 mM phthalate buffer.

Figure 2:
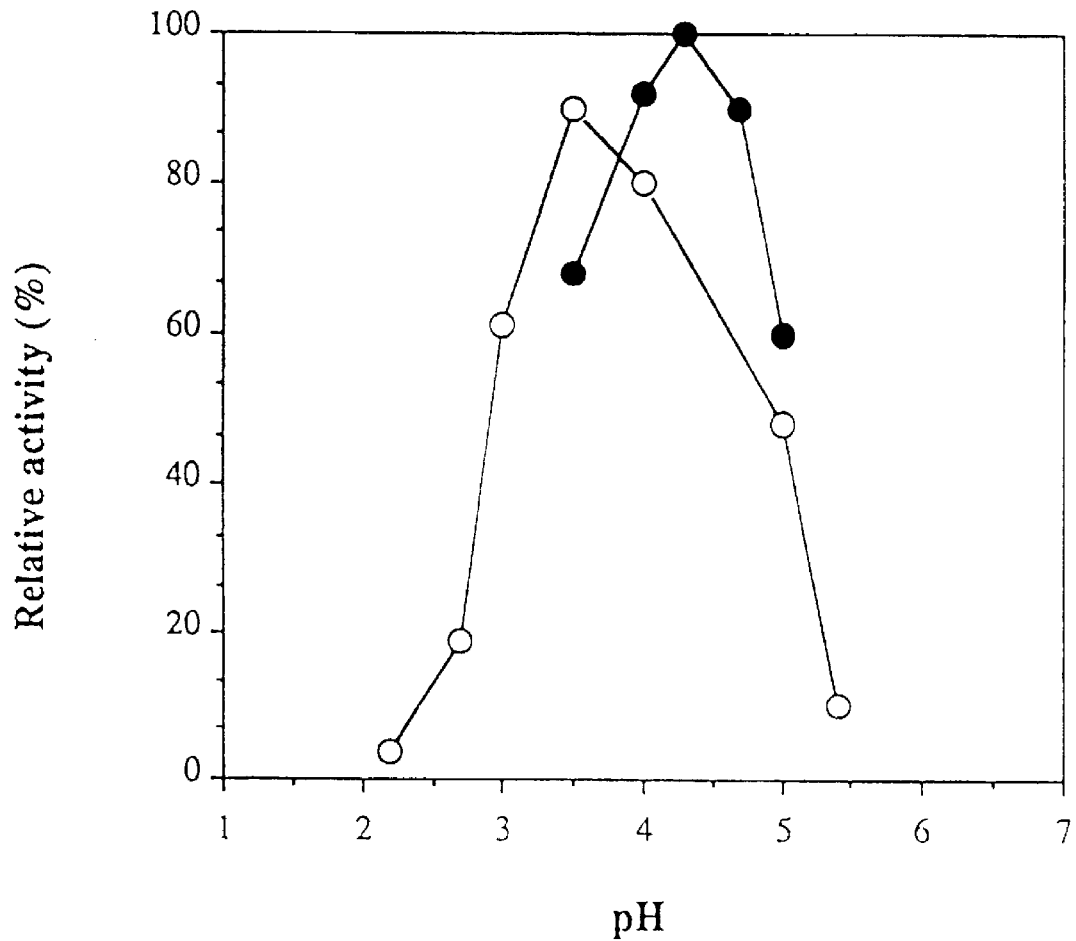
FIG. 2 shows the relative activity of purified phytase having a molecular size of 50 kD±5 kD originated from *Schwaniiomyces occidentalis*.

The results are shown in FIG. 2. In FIG. 2, the relative activity is defined taking the activity of the enzyme when the enzyme reaction is carried out in 20 mM sodium acetate buffer (pH 4.4) as 100%. In FIG. 2, the symbol "○" shows the results wherein 20 mM sodium acetate buffer was used and the symbol "●" shows the results wherein 20 mM phthalate buffer was used. As can be seen from FIG. 2, the optimum pH of this enzyme is between 2.7 and 5.0.

Figure 3:
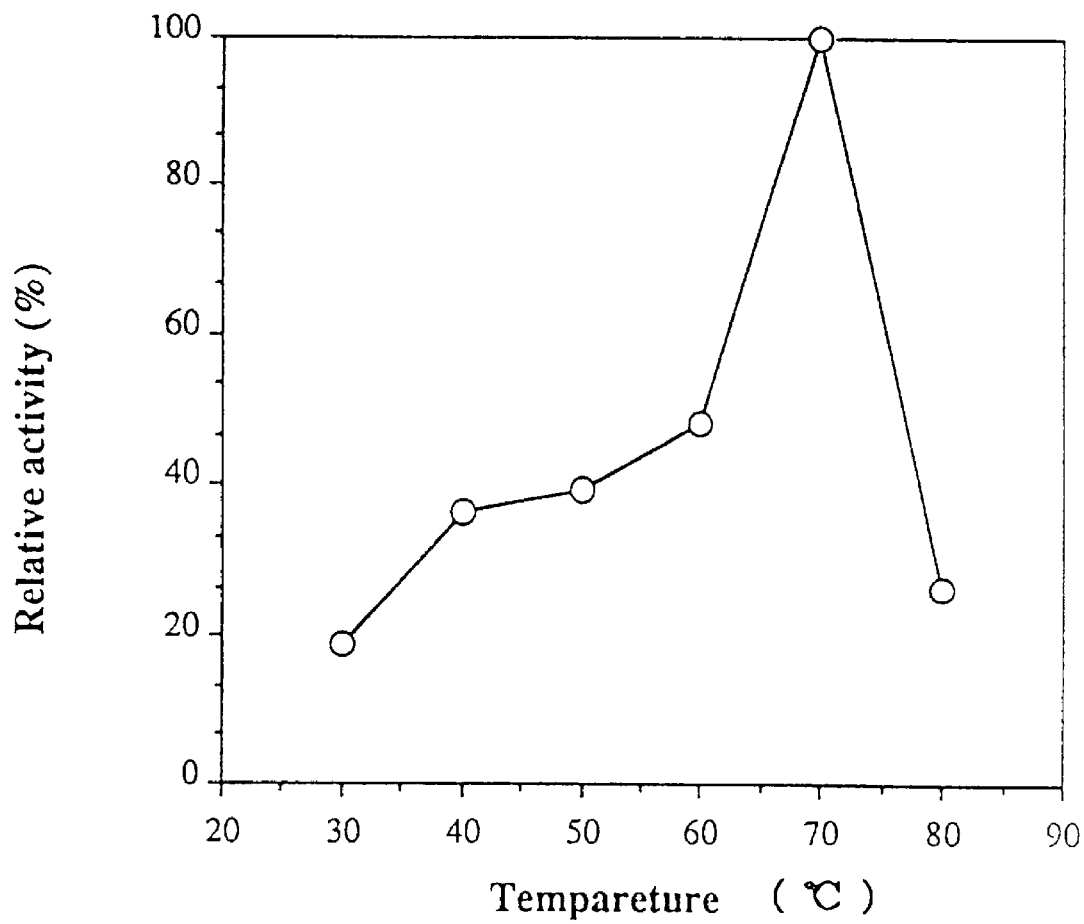
FIG. 3 shows temperature dependence of the activity of purified phytase having a molecular size of 50 kD±5 kD originated from *Schwaniiomyces occidentalis*.

The optimum temperature of the enzyme was measured by measuring the activity of the enzyme by the method described in Example 1, wherein the temperature during the enzyme reaction was changed. The results are shown in FIG. 3. In FIG. 3, the relative activity is defined taking the activity of the enzyme when the enzyme reaction is carried out at 70° C. As shown in FIG. 3, the optimum temperature of this enzyme is about 70° C.

Figure 4:
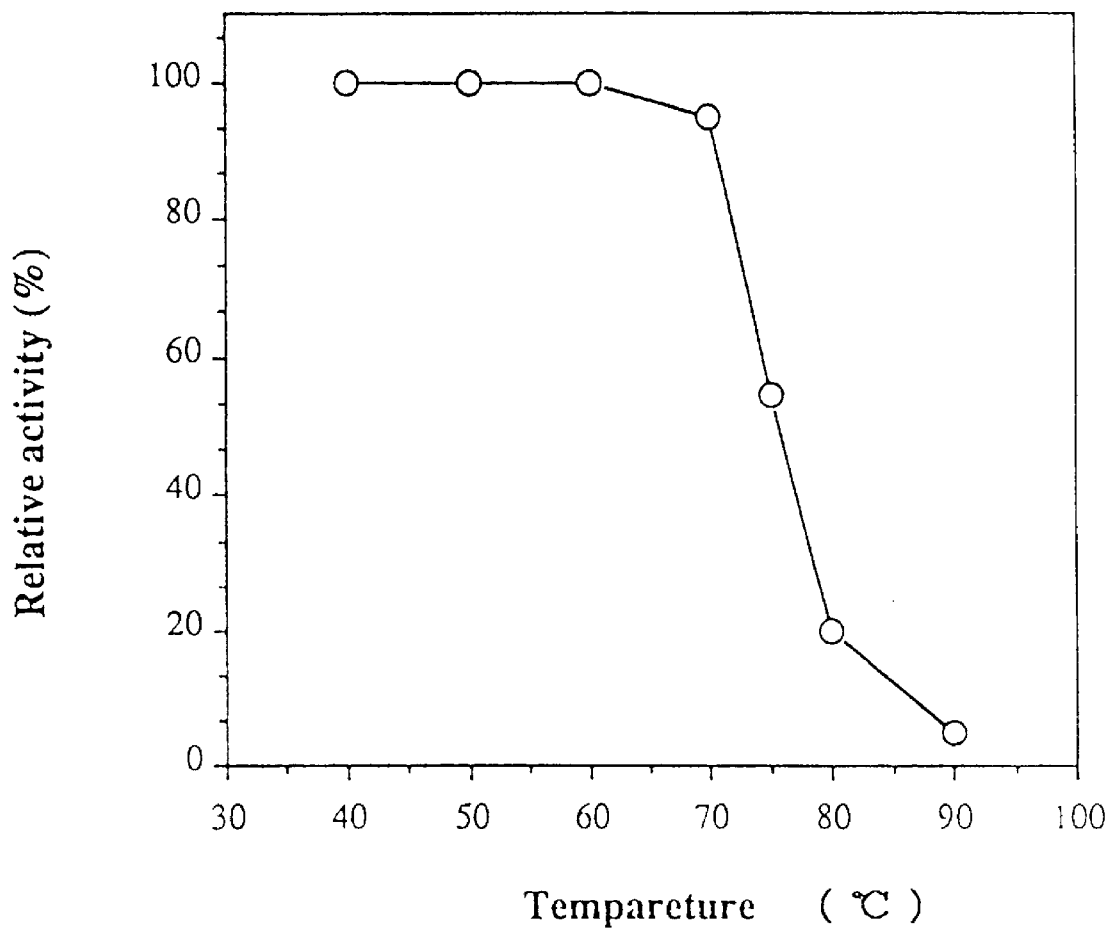
FIG. 4 shows heat resistance of purified phytase having a molecular size of 50 kD±5 kD originated from *Schwaniiomyces occidentalis*.

The heat resistance of the enzyme was determined by incubating the enzyme in 20 mM sodium acetate buffer (pH 4.4) for 30 minutes at varying temperature and the enzyme activity of the heat treated solution was measured by the method described in Example 1. The results are shown in FIG. 4. In FIG. 4, the relative activity is defined taking the activity of the enzyme before the incubation. As can be seen from FIG. 4, the residual activity of the enzyme was about 90% at 70° C. and about 50% at 75° C.

Example 4

Production of myo-inositol by Phytase

Figure 6:
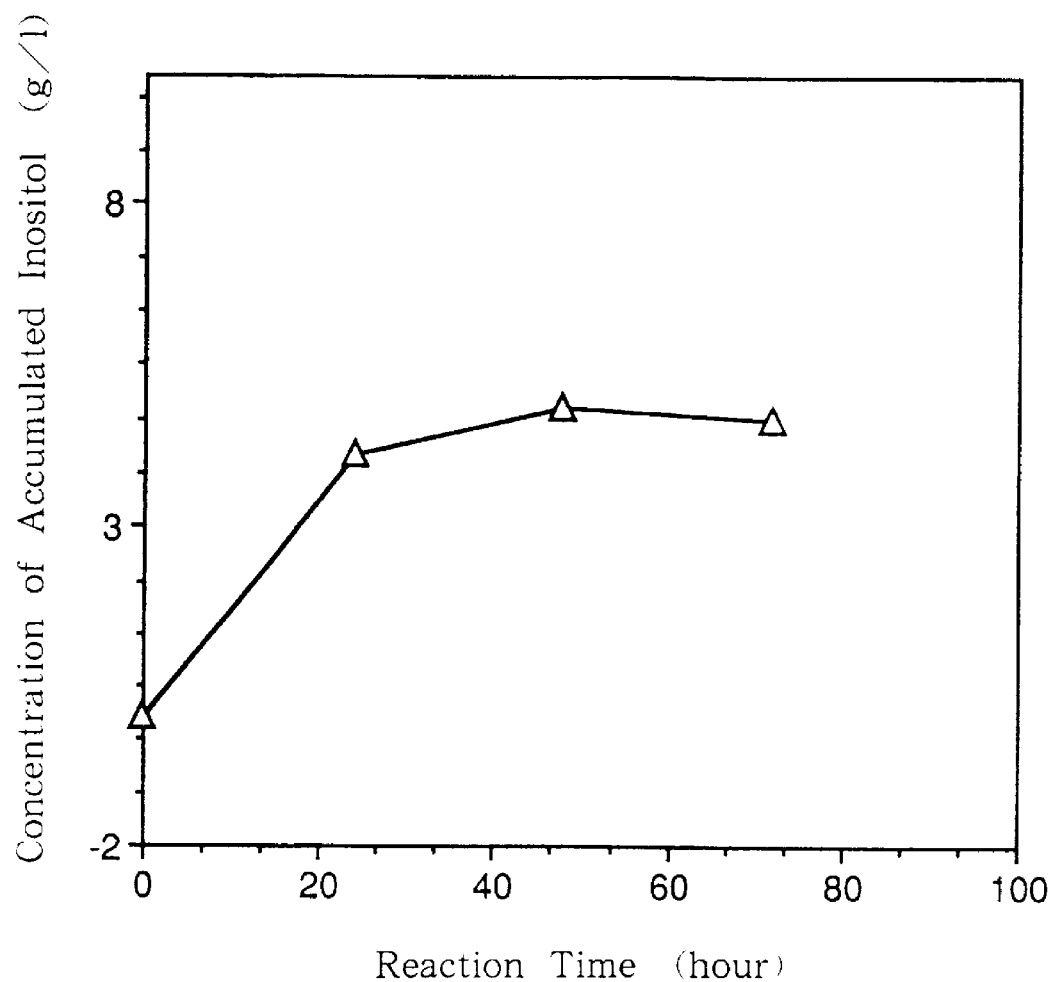
FIG. 6 shows change with time in the concentration of accumulated myo-inositol during the reaction employing the purified enzyme.

To a solution (pH 4.0) containing 100 g/l of calcium phytate, the purified phytase obtained in Example 3 was added to a concentration of 8 U/ml, and the mixture was allowed to react at 50° C. The accumulated myo-inositol was quantified by high performance liquid chromatography. The results are shown in FIG. 6.

Example 5

Determination of Amino Acid Sequence of N-terminal Region

The purified enzyme was treated with Endo H to remove sugar chains and the resultant was applied to Bio-Rad Prep-Cell Model 491 to eliminate those molecules in which removal of sugar chains was incomplete. The resulting enzyme was electrophoresed by 12.5% SDS-PAGE, and the pattern was electrophoretically transferred to a PVDF blotting membrane filter (IMMUNOVIRON, commercially available from Millipore) by a Sartorius blotting apparatus. After washing the membrane filter, the positions of proteins were determined based on coloring by Ponceau reagent. The band of interest was cut out and dried, and the sequence of the N-terminal region of the enzyme was determined by an amino acid sequencer (commercially available from Shimadzu Corp). The determined sequence is shown in SEQ ID. NO. 1 in Sequence Listing.

Example 6

Determination of Amino Acid Sequence of N-terminal Region of Partial Digest by V8 Protease The enzyme exhibiting a molecular size of 50 kD from which sugar chains were removed by the method described in Example 2 was dissolved in a sample buffer (125 mM Tris-HCl (pH 6.8) containing 0.1% SDS and 10% glycerol) in an amount of 200–400 μg. On the other hand, 1 μg of V8(Glu-c) protease originated from a microorganism belonging to genus Staphylococcus was dissolved in buffer for protease (125 mM Tris-HCl (pH 6.8) containing 0.1% SDS and 5% glycerol).

On 17% SDS-PAGE gel, the phytase solution was mounted and then the V8 protease solution was slowly overlaid. The resultant was electrophoresed. When the BPB marker reached the vicinity of the border between the stacking gel and the separation gel, the electrophoresis was stopped for 30 minutes, thereby allowing reaction between the protease and the phytase. Then electrophoresis was restarted and the sequence of the N-terminal region of the fragment resulting from the partial digestion of the phytase was determined by the method described in Example 4. The determined sequence is shown in SEQ ID NO. 2 in Sequence Listing.

Example 7

Screening of Phytase cDNA
(1) Preparation of Antibody

One hundred microliters of a solution (1 mg/ml) of the enzyme exhibiting a molecular size of 50 kD from which sugar chains were removed by the method described in Example 2(1) was mixed with 100 μl of Freund's complete adjuvant (commercially available from DIFCO) and the mixture was emulsified. The obtained emulsion was used as an immunogen.

The immunogen was subcutaneously administered to a rabbit in several times and booster was administered at 2, 4 and 6 weeks after the first immunization. The increase of the antibody titer was monitored by ELISA comparing the measured titer with the titer measured before the immunization.

After the above-described immunization, serum was recovered and the antibody was purified by affinity column prepared by coupling 1 mg of the purified phytase after the removal of sugar chains to 0.1 g of CNBr-activated Sepharose 4B (commercially available from Pharmacia).

Figure 7:
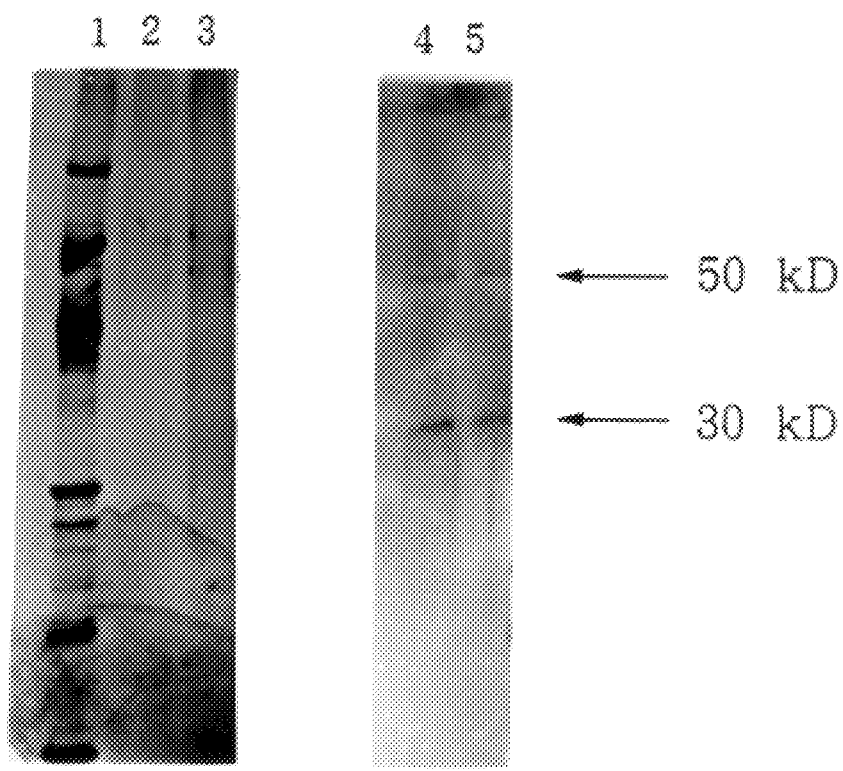
FIG. 7 shows the results of Western blot analysis of culture supernatant and cell debris of *Schwaniiomyces occidentalis*.

Using the thus purified antibody, Western blot analysis was performed on the crude enzyme after removing sugar chains. The results are shown in FIG. 7. In FIG. 7, lane 1 shows the electrophoretic pattern of molecular size Marker L (commercially available from BIORAD); lanes 2 and 3 show the SDS-PAGE patterns of the culture supernatant and cell debris, respectively; and lanes 4 and 5 show the results of Western blot analysis of the culture supernatant and cell debris, respectively, which were electrophoresed under the same conditions in the SDS-PAGE as those of lanes 2 and 3. As can be seen from FIG. 7, a band corresponding to a molecular size of 50 kD which is thought to be the band of the enzyme, and a band corresponding to a molecular size of 30 kD which is thought to be a fragment generated by decomposition of the enzyme were stained by the antibody.

(2) Cloning of Phytase cDNA

*Schwaniiomyces occidentalis* was cultured by the method described in Example 4 until absorbance at 660 nm reached 1.0. After collecting the cells by centrifugation, the cells were washed with sodium acetate buffer (pH 3.5) to remove precipitated $CaCO_3$ and then with 10 mM Tris-HCl pH 7.0.

The obtained cells were disrupted by freezing the cells by liquid nitrogen and grinding the frozen cells in a mortar together with sea sand. To the obtained powder, the extraction buffer of Quick Prep mRNA purification kit (commercially available from Pharmacia) was added and the resultant was uniformly mixed, followed by centrifugation at 4° C. at 2000 g. The supernatant was collected, thereby collecting the total RNAs. In accordance with the instructions of Quick Prep mRNA purification kit, mRNAs were recovered. Then cDNAs were synthesized using a commercially available kit (UniZAP cDNA Library kit (commercially available from STRATAGENE) and the obtained cDNAs were packaged using a commercially available kit (GIGAPACK GOLD II, STRATAGENE), thereby preparing a cDNA library.

The cDNAs were expressed by IPTG induction and the obtained 50,000 plaques were transferred to a PVDF blotting membrane filter (IMMUNOVIRON, commercially available from Millipore) in accordance with the instructions of UniZAP cDNA Library kit (commercially available from STRATAGENE), followed by screening with the antibody prepared above as a probe. The cDNA of the clone reacted with the antibody was subcloned into pBluescript SK- by in vivo excision. The obtained recombinant *Escherichia coli* MT-10743 was deposited in National Institute of Bioscience and Human-Technology, Agency of Industrial Science and Technology at 1–3, Higashi 1-chome, Tsukuba-shi, Ibaraki-ken, 305 Japan on Apr. 21, 1994 under accession No. FERM P-14287 and the deposition was converted to international deposition under the Budapest Treaty on May 25, 1995, under accession No. FERM BP-5108. The subcloned cDNA was sequenced and the determined nucleotide sequence was the same as that shown in SEQ ID NO. 5. In this nucleotide sequence, the nucleotide sequences shown in SEQ ID NOs. 3 and 4 are contained at 11–34 nt and 377–400 nt, respectively.

Example 8

Cloning of Phytase Genome DNA

One platinum loop of *Schwaniiomyces occidentalis* was inoculated to 5 ml of YEPD medium (containing 10% yeast extract, 20% polypeptone, 20% glucose) and the culture medium was incubated overnight at 30° C. The culture medium was then aseptically inoculated to 1 liter of YEPD medium. Culture was continued until the absorbance at 660 nm reached 5.0 and the culture medium was centrifuged at 2000×g to recover the cells. The obtained cells were suspended in 30 ml of lysis buffer (1M sorbitol, 25 mM EDTA, 50 mM MES (pH 5.5), 4 mg/ml of Novozyme 234 (commercially available from Novo Biolabs), 20 mg/ml of Zymolyase (commercially available from Seikagaku)) and the suspension was incubated at 30° C. for 1 hour. After confirming that the cells were converted to protoplasts, 500 µl of diethyl pyrocarbonate, 1.2 ml of 0.5M EDTA, 1.6 ml of 0.2M Tris base and 1.6 ml of 10% SDS were added and the resultant was well mixed, followed by incubation at 4° C. for 30 minutes.

Thereafter, 3.5 ml of 5M potassium acetate was added and the suspension was centrifuged at 2000 g for 10 minutes, followed by recovery of supernatant. The obtained supernatant was treated with equivolume of phenol/chloroform three times and then equivolume of 2-propanol was added, followed by incubation at −20° C. for 2 hours. After centrifugation at 3000 g for 10 minutes, the precipitate was washed twice with 70% ethanol and dried. The dried precipitate was dissolved in 2 ml of TE buffer and ¹⁄₁₀₀ volume of 1 mg/ml RNase was added to the solution, followed by incubation of the resulting mixture at 37° C. for 30 minutes.

The resulting solution was treated twice with equivolume of phenol/chloroform and ¹⁄₁₀ volume of 3M sodium acetate was added. To the resultant, twice volume of ethanol was added and the mixture was left to stand at −20° C. for 2 hours.

The obtained DNA was partially digested with a restriction enzyme Sau3AI, and a genome library was prepared from 9–23 kb fragments using a commercially available kit (LAMBDA EMBL 3/BamHI VECTOR KIT (commercially available from STRATAGENE)).

Using the thus prepared genome library, the fragment containing the gene encoding the phytase of interest was cloned in accordance with the instructions of LAMBDA EMBL 3/BamHI VECTOR KIT, STRATAGENE. In this procedure, the cDNA obtained in Example 7 was used as the probe.

Figure 8:
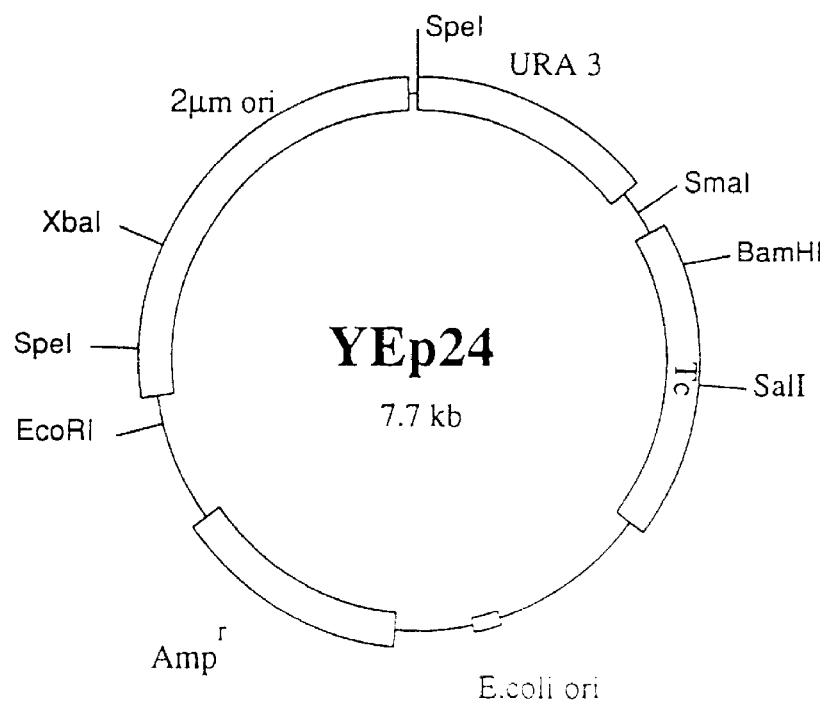
FIG. 8 shows plasmid maps of YEp24 and YEpGPH 1.
Figure 8:
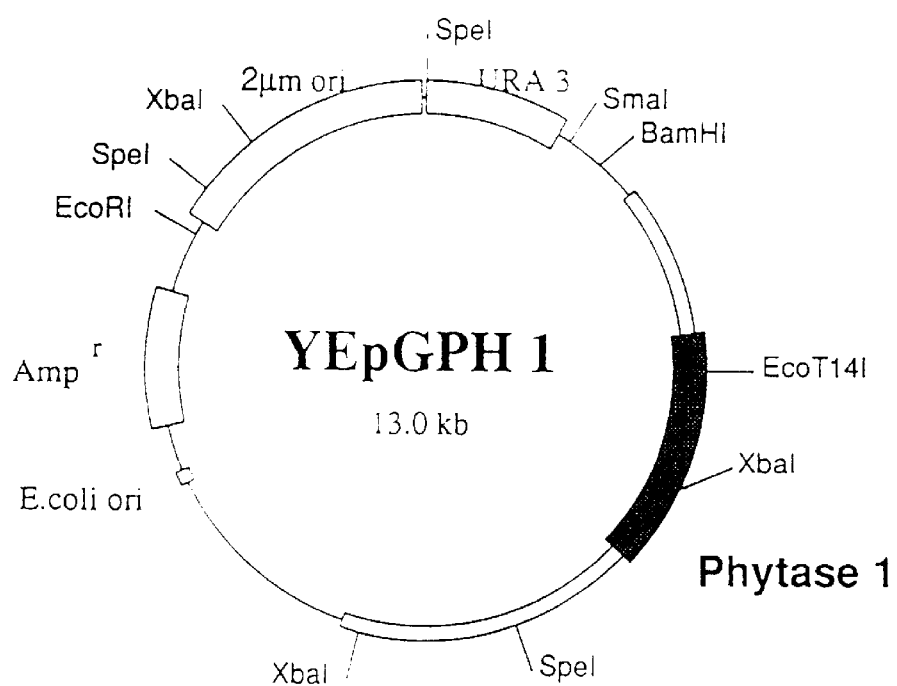

Among the obtained fragments, XhoI fragment of about 5.3 kb was subcloned into a vector plasmid YEp24 at SalI site to obtain a recombinant vector YEpGPH 1 (FIG. 8). The plasmid YEp24 was extracted from ATCC-37051 by a conventional method.

Example 9

Breeding of Yeast Secreting Phytase Originated from *Schwaniiomyces occidentalis*

In accordance with the method of Ito et al. (Ito, H., Y. Jukuda, K. Murata and A. Kimura, J. Bacteriol., Vol. 153, pp.163–168, (1983)), *Saccharomyces cerevisiae* W303-1B (Matα ade2-1 his3-11,15 leu2-3,112 ura3-1 trp1-1 can1-100) was transformed with the recombinant plasmid (YEpGPH 1) obtained in Example 8. As a result, a transformant MT-40539 was obtained, which was deposited in the above-mentioned National Institute of Bioscience and Human-Technology on May 25, 1994 under accession No. FERM P-14333 and the deposition was converted to international deposition under the Budapest Treaty on May 25, 1995, under accession No. FERM BP-5109.

Figure 9:
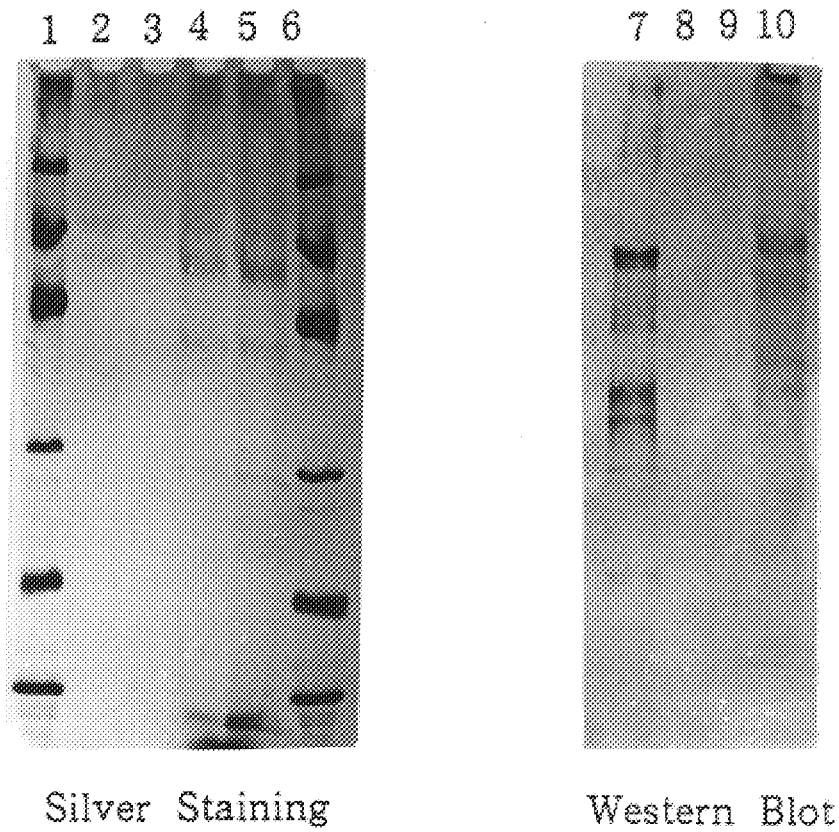
FIG. 9 shows the electrophoretic patterns of the culture supernatant of MT-40539 after silver staining or Western blot analysis.

The transformant MT-40539 and *Saccharomyces cerevisiae* W303-1B transformed with the vector plasmid YEp24 as a control were cultured in a medium described in Example 1 to which required nutrients (20 mg/l of adenine, 20 mg/l of histidine, 30 mg/l of leucine, 20 mg/l of tryptophan) had been added and the phytase activities of the cultured cells were measured. As a result, MT-40539 exhibited higher phytase activity than that exhibited by *Saccharomyces cerevisiae* W303-1B transformed with the vector plasmid YEp24. The culture supernatant was subjected to Western blot analysis using the antibody obtained in Example 7(1). As a result, a protein recognized by the antibody was detected. The pattern of the Western blot analysis is shown in FIG. 9. In FIG. 9, lanes 1 and 6 show electrophoretic patterns of molecular size Marker L (commercially available from BIORAD); lanes 2 and 7 show the patterns of phytase purified from culture supernatant of *Schwaniiomyces occidentalis*; lanes 3 and 8 are vacant lanes; lanes 4 and 9 show the patterns of the samples obtained by removing sugar chains of the phytase by Endo H, which was obtained from the culture supernatant of the transformants prepared by transforming *Saccharomyces cerevisiae* W303-1B with YEp24; and lanes 5 and 10 show the patterns of the samples obtained by removing sugar chains of the phytase by Endo H, which was obtained from the culture supernatant of MT-40539.

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Schwaniiomyces occidentalis
        ( C ) INDIVIDUAL ISOLATE: wild type ( i x ) FEATURE:
        ( A ) NAME/KEY: Peptide
        ( B ) LOCATION: 1..8
        ( D ) OTHER INFORMATION: /note= "N-terminal."

( x i ) SEQUENCE DESCRIPTION: SEQ ID NO:1:

Val  Ser  Ile  Ser  Lys  Leu  Ile  Asn
    1                        5

( 2 ) INFORMATION FOR SEQ ID NO:2:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Schwaniiomyces occidentalis
        ( C ) INDIVIDUAL ISOLATE: wild type ( i x ) FEATURE:
        ( A ) NAME/KEY: Peptide
        ( B ) LOCATION: 1..8
        ( D ) OTHER INFORMATION: /note= "N-terminal of fragment
                obtained by partial digestion with V8 protease."

( x i ) SEQUENCE DESCRIPTION: SEQ ID NO:2:

Thr  Ser  Ala  Leu  Asn  Ser  Gln  Gly
    1                        5

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:

(A) ORGANISM: Schwaniiomyces occidentalis
(C) INDIVIDUAL ISOLATE: wild type (x i) SEQUENCE DESCRIPTION: SEQ ID NO:3:

GTCTCGATCT CAAAATTAAT TAAT                                                    24

(2) INFORMATION FOR SEQ ID NO:4:

(i) SEQUENCE CHARACTERISTICS:
(A) LENGTH: 24 base pairs
(B) TYPE: nucleic acid
(C) STRANDEDNESS: double
(D) TOPOLOGY: linear (i i) MOLECULE TYPE: cDNA (v i) ORIGINAL SOURCE:
(A) ORGANISM: Schwaniiomyces occidentalis
(C) INDIVIDUAL ISOLATE: wild type (x i) SEQUENCE DESCRIPTION: SEQ ID NO:4:

ACAAGTGCAC TGAACTCGCA AGGT                                                    24

(2) INFORMATION FOR SEQ ID NO:5:

(i) SEQUENCE CHARACTERISTICS:
(A) LENGTH: 1631 base pairs
(B) TYPE: nucleic acid
(C) STRANDEDNESS: double
(D) TOPOLOGY: linear (i i) MOLECULE TYPE: cDNA (v i) ORIGINAL SOURCE:
(A) ORGANISM: Schwaniiomyces occidentalis
(C) INDIVIDUAL ISOLATE: wild type (i x) FEATURE:
(A) NAME/KEY: CDS
(B) LOCATION: 8..1390

(x i) SEQUENCE DESCRIPTION: SEQ ID NO:5:

```
GTCAATC ATG GTC TCG ATC TCA AAA TTA ATT AAT AAC GGT TTA CTC TTA              49
        Met Val Ser Ile Ser Lys Leu Ile Asn Asn Gly Leu Leu Leu
        1               5                   10

GCT GGT CAA AGT GTT TAC CAA GAT TTA GCT ACT CCA CAA CAA TCT TCC               97
Ala Gly Gln Ser Val Tyr Gln Asp Leu Ala Thr Pro Gln Gln Ser Ser
15              20                  25                  30

GTC GAG CAG TAT AAT ATT ATT AGG TTT TTA GGT GGT TCG GGT CCT TAC              145
Val Glu Gln Tyr Asn Ile Ile Arg Phe Leu Gly Gly Ser Gly Pro Tyr
                35                  40                  45

ATT CAA CGC AGT GGT TAT GGT ATT TCC ACT GAT ATT CCT GAT CAG TGC              193
Ile Gln Arg Ser Gly Tyr Gly Ile Ser Thr Asp Ile Pro Asp Gln Cys
            50                  55                  60

ACA ATT AAG CAA GTT CAG TTG ATG TCA AGG CAT GGG GAA AGA TAC CCT              241
Thr Ile Lys Gln Val Gln Leu Met Ser Arg His Gly Glu Arg Tyr Pro
        65                  70                  75

TCA AAA AAC TCT GGT AAG AAG TTA AAA ACA ATA TAT GGT AAA TTA AAG              289
Ser Lys Asn Ser Gly Lys Lys Leu Lys Thr Ile Tyr Gly Lys Leu Lys
    80                  85                  90

AGC TAC AAT GGC ACT TTC ACA GGT AGC TTA GCT TTT TTG AAT GAC TAT              337
Ser Tyr Asn Gly Thr Phe Thr Gly Ser Leu Ala Phe Leu Asn Asp Tyr
95                  100                 105                 110

GAA TAT TTT GTT CCG GAT GAT AGT TTG TAC GAA AAG GAA ACA AGT GCA              385
Glu Tyr Phe Val Pro Asp Asp Ser Leu Tyr Glu Lys Glu Thr Ser Ala
                115                 120                 125

CTG AAC TCG CAA GGT TTA TTT GCA GGT ACT ACA GAT GCC TTA AGA CAT              433
```

-continued

| | | | | | | | | | | | | | | |
|---|---|---|---|---|---|---|---|---|---|---|---|---|---|---|
|Leu|Asn|Ser|Gln|Gly|Leu|Phe|Ala|Gly|Thr|Thr|Asp|Ala|Leu|Arg|His|
| | |130| | | |135| | | | |140| | | |

```
      GGT  GCT  GCT  TTT  AGA  GCT  AAA  TAT  GGA  TCA  TTG  TAT  AAA  CAA  AAT  TCT      481
      Gly  Ala  Ala  Phe  Arg  Ala  Lys  Tyr  Gly  Ser  Leu  Tyr  Lys  Gln  Asn  Ser
                145                     150                     155

ACC  TTG  CCA  GTT  TTC  ACT  TCA  AAT  TCC  AAC  AGA  GTC  TAC  CAG  ACT  TCT           529
Thr  Leu  Pro  Val  Phe  Thr  Ser  Asn  Ser  Asn  Arg  Val  Tyr  Gln  Thr  Ser
     160                     165                     170

GAA  TAC  TTT  GCC  AGA  GGT  TTC  TTA  GGT  GAT  GAA  TTT  TCT  GAT  GCT  ACT           577
Glu  Tyr  Phe  Ala  Arg  Gly  Phe  Leu  Gly  Asp  Glu  Phe  Ser  Asp  Ala  Thr
175                     180                     185                     190

GTT  CAC  TTT  GCT  ATC  ATT  GAT  GAA  GAC  CCT  AAA  ATG  GGT  GTT  AAT  TCA           625
Val  His  Phe  Ala  Ile  Ile  Asp  Glu  Asp  Pro  Lys  Met  Gly  Val  Asn  Ser
                195                     200                     205

TTA  ACA  CCA  AGA  GCC  GCT  TGT  GAC  AAT  TAT  AAT  GAG  GAT  GTG  AAT  GAC           673
Leu  Thr  Pro  Arg  Ala  Ala  Cys  Asp  Asn  Tyr  Asn  Glu  Asp  Val  Asn  Asp
               210                     215                     220

GGC  ATT  GTC  AAT  CAA  TAT  AGC  ACT  GAC  TAT  TTG  GAT  GAA  GCC  CTT  AAA           721
Gly  Ile  Val  Asn  Gln  Tyr  Ser  Thr  Asp  Tyr  Leu  Asp  Glu  Ala  Leu  Lys
               225                     230                     235

AGA  TTC  CAA  TCA  TCA  AAT  CCA  GGA  TTG  AAT  TTG  ACC  TCG  GAA  GAC  GTT           769
Arg  Phe  Gln  Ser  Ser  Asn  Pro  Gly  Leu  Asn  Leu  Thr  Ser  Glu  Asp  Val
     240                     245                     250

TAC  CAA  CTT  TTC  GCT  TAC  TGT  GCA  TAT  GAG  ACT  AAT  GTT  AAG  GGT  GCA           817
Tyr  Gln  Leu  Phe  Ala  Tyr  Cys  Ala  Tyr  Glu  Thr  Asn  Val  Lys  Gly  Ala
255                     260                     265                     270

TCC  CCA  TTC  TGT  GAC  TTA  TTT  ACT  AAT  GAA  GAA  TAC  ATT  CAA  TAT  TCC           865
Ser  Pro  Phe  Cys  Asp  Leu  Phe  Thr  Asn  Glu  Glu  Tyr  Ile  Gln  Tyr  Ser
                275                     280                     285

TAC  AGC  GTT  GAT  CTT  TCT  AAT  TAT  TAT  TCT  CAC  GGG  GCA  GGT  CAT  AAT           913
Tyr  Ser  Val  Asp  Leu  Ser  Asn  Tyr  Tyr  Ser  His  Gly  Ala  Gly  His  Asn
               290                     295                     300

CTA  ACT  AAA  ACC  ATT  GGT  TCT  ACT  TTA  TTA  AAT  GCC  TCA  TTA  ACC  TTA           961
Leu  Thr  Lys  Thr  Ile  Gly  Ser  Thr  Leu  Leu  Asn  Ala  Ser  Leu  Thr  Leu
          305                     310                     315

TTA  AAA  GAT  GGC  ACC  AAT  GAC  AAT  AAA  ATC  TGG  TTA  TCT  TTT  TCA  CAC          1009
Leu  Lys  Asp  Gly  Thr  Asn  Asp  Asn  Lys  Ile  Trp  Leu  Ser  Phe  Ser  His
     320                     325                     330

GAT  ACT  GAT  TTG  GAA  ATC  TTC  CAT  AGT  GCC  TTA  GGA  ATT  GTT  GAG  CCA          1057
Asp  Thr  Asp  Leu  Glu  Ile  Phe  His  Ser  Ala  Leu  Gly  Ile  Val  Glu  Pro
335                     340                     345                     350

GCT  GAA  GAT  TTA  CCA  GTT  GAT  TAC  ATT  CCT  TTT  CCA  TCG  CCA  TAT  ATT          1105
Ala  Glu  Asp  Leu  Pro  Val  Asp  Tyr  Ile  Pro  Phe  Pro  Ser  Pro  Tyr  Ile
                355                     360                     365

CAC  TCA  CAA  ATT  GTT  CCA  CAA  GGT  GCT  AGA  ATT  TAT  ACT  GAG  AAA  TAT          1153
His  Ser  Gln  Ile  Val  Pro  Gln  Gly  Ala  Arg  Ile  Tyr  Thr  Glu  Lys  Tyr
               370                     375                     380

TCA  TGT  GGC  AAC  GAA  ACC  TAT  GTT  AGA  TAT  ATA  CTT  AAT  GAT  GCA  GTT          1201
Ser  Cys  Gly  Asn  Glu  Thr  Tyr  Val  Arg  Tyr  Ile  Leu  Asn  Asp  Ala  Val
          385                     390                     395

GTT  CCA  ATT  CCA  AAA  TGC  TCT  TCT  GGT  CCA  GGG  TTC  TCA  TGT  GAG  CTT          1249
Val  Pro  Ile  Pro  Lys  Cys  Ser  Ser  Gly  Pro  Gly  Phe  Ser  Cys  Glu  Leu
     400                     405                     410

AGT  AAA  TTC  GAA  GAA  TAT  ATT  AAT  AAA  AGA  CTT  AGG  GAT  GTT  GAC  TTT          1297
Ser  Lys  Phe  Glu  Glu  Tyr  Ile  Asn  Lys  Arg  Leu  Arg  Asp  Val  Asp  Phe
415                     420                     425                     430

GTT  GAA  CAA  TGT  GAT  TTA  AAA  GAT  GCT  CCA  ACT  GAA  GTT  ACT  TTT  TAC          1345
Val  Glu  Gln  Cys  Asp  Leu  Lys  Asp  Ala  Pro  Thr  Glu  Val  Thr  Phe  Tyr
                435                     440                     445

TGG  GAT  TAC  ACG  TCG  GTG  AAC  TAT  AGT  GCG  TCC  CTT  ATT  AAT  GGT               1390
```

| Trp | Asp | Tyr | Thr | Ser | Val | Asn | Tyr | Ser | Ala | Ser | Leu | Ile | Asn | Gly |
|-----|-----|-----|-----|-----|-----|-----|-----|-----|-----|-----|-----|-----|-----|-----|
|     |     |     | 450 |     |     |     |     | 455 |     |     |     |     | 460 |     |

| | | | | | |
|---|---|---|---|---|---|
| TAAATTGAGT | ATAGGAGAAT | ATCTTATTTC | TAGTTTGATC | ACTATCTGAA | TCCACTTTGC | 1450 |
| TCTTTCTCCT | TGTTTTGATT | GCTTATCCAT | TGTTTAGAAA | TACGTTATAA | AGCAATCATT | 1510 |
| TTTACAACTA | TGTCGTCTAA | TACTTTGTTT | CTAGAATTAA | AAAAATAAAT | AGTATACCTG | 1570 |
| TGTAAAGTCT | TACTTGATAG | CTAACTAGTC | ACTTCTTAAT | CATACACCTA | ATCTATCCTA | 1630 |
| A | | | | | | 1631 |

We claim:

1. A cloned gene originated from *Schwanniomyces occidentalis*, which encodes a single type of phytase subunit having a molecular size after removing sugar chains of 50 kD±5 kD determined by SDS-polyacrylamide gel electrophoresis.

2. The gene according to claim 1, which encodes the amino acid sequence shown in SEQ ID NO. 5.

3. The gene according to claim 1, which contains at least one DNA sequence having a nucleotide sequence shown in SEQ ID NO. 3, SEQ ID NO. 4 or SEQ ID NO. 5.

4. The gene according to claim 3, which has the nucleotide sequence shown in SEQ ID NO. 5.

5. A recombinant vector containing the phytase gene according to claim 1, said recombinant vector can express said gene in a host cell.

6. The recombinant vector according to claim 5, which is YEpGPH 1.

7. A microorganism transformed with said recombinant vector according to claim 5.

8. The microorganism according to claim 7, which is *Escherichia coli*.

9. The recombinant *Escherichia coli* which is *Escherichia coli*, of FERM BP-5108.

10. The microorganism according to claim 7, which is a yeast cell.

11. The microorganism according to claim 10, which is *Saccharomyces cerevisiae* FERM BP-5109.

12. A culture medium containing the recombinant microorganism according to claim 7.

13. A method for converting a phytate to myo-inositol comprising: contacting the phytate with an effective amount of the recombinant microorganism or the culture medium containing the recombinant microorganism, wherein the said microorganism is that of claim 7.

* * * * *

UNITED STATES PATENT AND TRADEMARK OFFICE
CERTIFICATE OF CORRECTION

PATENT NO. : 5,840,561

DATED: : November 24, 1998

INVENTOR(S) : Daisuki MOCHISUKI et al.

It is certified that error appears in the above-identified patent and that said Letters Patent is hereby corrected as shown below:

On page 1, column 1, in the inventive entity, please delete "Tokudo" and insert

--Tokuda--;

On page 1, column 1, in the references cited, please add the following references

| | | |
|---|---|---|
| --0 321004 B1 | 1/92 | EPO |
| 0 420358 A1 | 4/91 | EPO |
| 93/16175 | 8/93 | WIPO |
| 94/03612 | 94 | WIPO |

*N.C. Mandal et al.*, Phytochemistry, vol. 11: pp. 495-502 (1972)

*P.E. Lim et al.*, Biochimica et Biophysica Acta, vol. 302: pp. 316-328 (1973)

*G.C.J. Irving et al.*, Aust. J. Biol. Sci., vol. 24: pp. 547-557 (1971)

*V.K. Powar et al.*, J. Bacteriolology, vol. 151, No. 3: pp. 1102-1109 (1982)

*Varsha Shah et al.*, Indian Journal of Biochemistry and Biophysics, vol. 27: pp. 98-102 (1990)

UNITED STATES PATENT AND TRADEMARK OFFICE
CERTIFICATE OF CORRECTION

PATENT NO. : 5,840,561

DATED: : November 24, 1998

INVENTOR(S) : Daisuki MOCHIZUKI et al.

It is certified that error appears in the above-identified patent and that said Letters Patent is hereby corrected as shown below:

Abul H.J. Ullah et al., Preparative Biochemistry, vol. 17(1): pp. 63-91 (1987)

P. Galzy et al., J. Fermentation Bioengineering, vol. 74, 1: pp. 7-11 (1992)

E. Graf et al., J. Am. Oil. Chem. Soc., vol. 60, No. 11: pp. 1861-1867 (1983)

Abul H.J. Ullah et al., Preparative Biochemistry, vol. 18(4): pp. 483-489 (1988)

Kregerm van Rij et al., the yeast, a taxonomic study, 3rd ed. Elsevier Sci. Publisher, Amsterday, The Netherlands (1984)

LIST OF CULTURE MICROORGANISMS, 9th ed.: Institute for Fermentation Osaka (IFO), pp. 75-76 (1992)

Ito, H., et al., J. Bacteriol., 153: pp. 163-168 (1983)

Greiner et al, "PURIFICATION AND CHARACTERIZATION OF TWO PHYTASES FROM ESCHERICHIA COLI", Archives of Biochemistry and Biophysics, Vol. 303, No. 1, pp. 107-113, 1993.

Houde et al, "PURIFICATION AND CHARACTERIZATION OF CANOLA SEED (BRASSICA sp.) PHYTASE", Journal of Food Biochemistry, Vol. 14, pp. 331-351, 1990.

Yamamoto et al, "CHEMICAL AND PHYSICOCHEMICAL PROPERTIES OF PHYTASE FROM ASPERGILLUS TERREUS", Agri. Biol. Chem., Vol. 36, No. 12, pp. 2097-2103, 1972.

UNITED STATES PATENT AND TRADEMARK OFFICE
CERTIFICATE OF CORRECTION

PATENT NO. : 5,840,561

DATED: : November 24, 1998

INVENTOR(S) : Daisuki MOCHIZUKI et al.

It is certified that error appears in the above-identified patent and that said Letters Patent is hereby corrected as shown below:

Hayakawa et al, "PURIFICATION AND CHARACTERIZATION OF ACID PHOSPHATASES WITH OR WITHOUT PHYTASE ACTIVITY FROM RICE BRAN", Agri Biol. Chem., Vol. 53, No. 6, pp. 1475-1483, 1989.--

On page 1, column 2, delete "Sequeilha et al." and insert --Segueilha et al.--.

In column 20, claim 9, line 1, after "*coli*" insert --of claim 8--; and
line 2, after "*coli*" delete "of".

Signed and Sealed this

Twenty-fourth Day of October, 2000

*Attest:*

Q. TODD DICKINSON

*Attesting Officer*     *Director of Patents and Trademarks*